US005546935A

United States Patent [19]
Champeau

[11] Patent Number: 5,546,935
[45] Date of Patent: Aug. 20, 1996

[54] ENDOTRACHEAL TUBE MOUNTED PRESSURE TRANSDUCER

[75] Inventor: Eugene J. Champeau, Plymouth, Minn.

[73] Assignee: MedAmicus, Inc., Minneapolis, Minn.

[21] Appl. No.: 28,355

[22] Filed: Mar. 9, 1993

[51] Int. Cl.$^6$ .......................... A61M 16/00; A62B 7/00; A62B 9/06; F16K 31/02

[52] U.S. Cl. ................ 128/205.23; 128/204.23; 128/207.14; 128/207.15

[58] Field of Search ...................... 128/716, 719, 128/675, 632, 635, 204.23, 206.29, 207.14, 207.15, 205.23; 604/45

[56] References Cited

U.S. PATENT DOCUMENTS

| | | | |
|---|---|---|---|
| 3,788,326 | 1/1974 | Jacobs | 128/207.15 |
| 3,893,451 | 7/1975 | Durand et al. | 128/673 |
| 4,141,356 | 2/1979 | Smargiassi | 128/DIG. 17 |
| 4,155,356 | 5/1979 | Venegas | 128/204.23 |
| 4,214,593 | 7/1980 | Imbruce et al. | 128/748 |
| 4,252,131 | 2/1981 | Hon et al. | 128/748 |
| 4,346,584 | 8/1982 | Boehringer | 73/23 |
| 4,387,711 | 6/1983 | Merry | 128/207.15 |
| 4,484,585 | 11/1984 | Baier | 128/748 |
| 4,487,206 | 12/1984 | Aagard | 128/667 |
| 4,502,490 | 3/1985 | Evans et al. | 128/780 |
| 4,509,370 | 4/1985 | Hirschfeld | 128/675 X |
| 4,535,766 | 8/1985 | Baum | 128/204.23 |
| 4,565,194 | 1/1986 | Weerda et al. | 128/204.23 |
| 4,621,646 | 11/1986 | Bryant | 128/692 |
| 4,635,631 | 1/1987 | Izumi | 128/204.23 |
| 4,672,974 | 6/1987 | Lee | 128/673 |
| 4,681,099 | 7/1987 | Sato et al. | 128/204.23 |
| 4,711,246 | 12/1987 | Alderson | 128/667 |
| 4,722,348 | 2/1988 | Ligtenberg | 128/675 |
| 4,735,212 | 4/1988 | Cohen | 128/667 |
| 4,813,431 | 3/1989 | Brown | 128/748 |
| 4,872,483 | 10/1989 | Shah | 137/557 |

(List continued on next page.)

OTHER PUBLICATIONS

"Sheridan/HVT; Sheridan/CF; Sheridan/Uncuffed", 1 p., Copyright 1988.
"Spiral–Flex Reinforced Tracheal Tube", 1 p., Patent date 1986.
"Sheridan Sher–I–Bronch", 1 p., Copyright 1988.
"Sheridan Flexibend Oral/Nasal Tracheal Tube", 1 p., Copyright 1988.
"Infant Star High Frequency Ventilator", 4 pp., Revision date Sep. 1990.
"Star Sync Patient Triggered Interface", 2 pp., Revision date Feb. 1991.

*Primary Examiner*—Kimberly L. Asher
*Attorney, Agent, or Firm*—Moore & Hansen

[57] ABSTRACT

The present invention provides an endotracheal breathing tube useful in patient ventilation that has a distally mounted pressure sensor transducer. The endotracheal breathing tube of the present invention has distal and proximal ends with the distal end being configured for emplacement at a preselected area of a patient's trachea and further has multiple interior passages with a first passage useful for providing a flow path for ventilation therapy gas being provided to the ventilated patient and for providing a flow path for removal of exhalation gases. A second passage is utilized by a pair of optical fibers for optical signal transmission to and from a pressure transducer disposed within the second passage near the distal end of the breathing tube. The second passage and the first passage communicate through an opening between the two passages such that the pressure transducer is exposed to the pressure within the distal end of the endotracheal breathing tube, which in turn is substantially equal to the gas pressure outside the endotracheal tube and thus to the gas pressure at the bronchi of the patient. The gas pressure sensed by the pressure transducer and any changes therein are transmitted substantially instantaneously to a ventilator that calculates the instantaneous pressure and provides a real time sensing of the pressure in the patient's lungs and any subsequent changes therein.

17 Claims, 5 Drawing Sheets

U.S. PATENT DOCUMENTS

| | | | |
|---|---|---|---|
| 4,960,411 | 10/1990 | Buchbinder | 128/657 X |
| 4,966,141 | 10/1990 | Bacaner | 128/207.14 |
| 4,971,034 | 11/1990 | Doi et al. | 128/6 |
| 5,005,584 | 4/1991 | Little | 128/748 |
| 5,024,219 | 6/1991 | Dietz | 128/204.23 |
| 5,038,771 | 8/1991 | Dietz | 128/204.23 |
| 5,056,513 | 10/1991 | Boutin | 128/204.23 |
| 5,074,299 | 12/1991 | Dietz | 128/204.23 |
| 5,161,525 | 11/1992 | Kimm et al. | 128/204.26 |

ENDOTRACHEAL TUBE MOUNTED PRESSURE TRANSDUCER

The present invention relates in general to apparatus for sensing pressure in a patient's body and in particular to a distally mounted endotracheal tube pressure transducer.

BACKGROUND OF THE PRESENT INVENTION

Providing respiratory or ventilation therapy to a patient is a well known medical procedure intended to aid in the stabilization and recovery of the patient. This therapy is often provided in surgical and critical care situations. Typically, an endotracheal breathing tube is inserted into the patient's mouth and then into their trachea so that the distal end of the breathing tube is disposed in the trachea before it branches into the bronchi that lead to the lungs. The proximal end of the breathing tube is usually connected to an airway tube that leads to a controllable gas supply delivery system—the ventilator. The ventilation therapy gas may be pure oxygen, atmospheric air mixed with the oxygen, and/or medication mixed with either oxygen or oxygen and air. The breathing and airway tubes thus serve as primary intake and exhaust pathways for inhalation and exhalation gases entering and leaving, respectively, the patient's body through the lungs. In this way the attending physician or clinician can closely monitor the functioning of the patient's respiratory system, particularly, and the overall health and well-being of the patient, generally.

When a balloon cuff is used the patient is dependent upon the ventilation apparatus to be able to breathe. Thus, if the ventilator responds slowly when the patient begins to inhale, the patient will be forced to breathe initially on his own against the ventilator since no air mixture is being supplied thereby; that is, there is no ventilation therapy gas flow from the ventilator. Similarly, if the ventilator responds slowly when the patient begins to exhale, the patient may be forcing exhalation gases from his lungs against the supplied ventilation therapy gas pressure. In either situation, this can be extremely tiring to a patient who is already in a weakened condition. The patient is forced to generate and expend a significant amount of energy working against the ventilator. This phenomenon is known as patient/ventilator asynchrony.

Some of the presently available ventilator models attempt to diminish the effects of patient/ventilator asynchrony by relying upon an abdominal triggering sensor to facilitate the supply and exhaust of gas to and from the patient's body. These models rely upon a sensor disposed near the patient's abdomen to sense abdominal movements supposedly indicative of inhalation and exhalations of the patient, and to begin and terminate ventilation therapy gas flow in response to the sensed abdominal movements. Other known ventilators may rely upon a prediction control method and apparatus that utilizes a learning function in order for the ventilator to "know" when to supply air to the patient. Neither type of ventilator is completely successful at reducing the patient fatigue caused by patient/ventilator asynchrony.

In addition to the fatigue induced by patient/ventilator asynchrony, damage known as barotrauma can occur to the lungs through over pressurization of the ventilation therapy gas supplied to the patient through the breathing tube. Because of this potential for lung damage, the gas pressure is usually monitored, often at a location within the breathing apparatus outside the patient's body. Known pressure sensing devices are installed in the ventilator and pressures in the airway and breathing tube are transported to the ventilator for measurement of the pressures at the proximal end of the breathing tube. These known pressure sensing devices provide a feedback signal of the pressure to a pressure regulator within the ventilator so that the pressure of the gas supplied through the breathing tube can be regulated.

Each of the present airway pressure sensing technologies suffers from several deficiencies. Among them is the inaccuracies between pressures registered at the ventilator and actual pressures within the lungs. These inaccuracies can lead to the aforementioned possibility of barotrauma to the alveoli of the lungs, particularly those of infants, due to the ventilation therapy gas being supplied to the patient at excessive pressures. These inaccuracies are partly due to inherent pressure gradients within the breathing circuit between the lungs and the location of the pressure sensor and partly to delays in the pressure sensing and response times of the ventilation equipment to excessive pressures. Because known technologies rely upon the transmission of changes in the gas pressure in the lungs to a location outside the lungs, the transmission occurring as a pressure wave being propagated down a tube, the speed of the propagation of that pressure wave determines the speed at which the ventilating equipment can respond. Additionally, because of those inherent delays in the sensing technologies currently being used, the energy required of the patient during respiration is greater than it would be if the signaling were more rapid, that is, if the aforementioned breathing circuit signal delays did not exist, since the patient is required to inhale and exhale against the ventilator—the patient/ventilator asynchrony problem. Finally, when the patient is forced to work against the ventilator, the effectiveness of the ventilation therapy is reduced because the percentage of the lung alveoli being ventilated is reduced from the optimum.

It would be desirable to have a patient ventilator that provided in situ sensing of the ventilated gas pressure as close as possible to the patient's lungs, that reduced or eliminated breathing circuit signal filtering delays, that allowed for rapid breath activation and triggering of the ventilation apparatus, that reduced the work of the patient in breathing, and that increased the effective alveolar ventilating volume.

SUMMARY OF THE PRESENT INVENTION

It is an object of the present invention to provide new and improved apparatus that is not subject to the foregoing disadvantages.

It is another object of the present invention to provide apparatus that will accurately sense the gas pressure within the lower end of a patient's trachea.

It is a further object of the present invention to provide new and improved apparatus that will reduce the transmission time of a sensed gas pressure within a patient's trachea to a ventilator.

It is still yet another object of the present invention to provide apparatus that will reduce the workload placed upon a patient using a ventilator by providing for rapid triggering of the ventilator in response to the inhalation and exhalation of the patient.

It is another object of the present invention to provide apparatus that will improve the performance of ventilation devices and reduce the risk of over-pressurization of a patient's lungs.

It is still another object of the present invention to provide new and improved apparatus that increases the effective alveolar ventilating volume.

There is provided by the present invention an improved endotracheal breathing tube having a distally mounted pressure sensor transducer useful in patient ventilation that is not subject to the foregoing disadvantages of the known prior art patient gas pressure sensing technologies. The improved endotracheal breathing tube of the present invention has distal and proximal ends with the distal end being configured for emplacement at a preselected area of a patient's trachea, normally just where the trachea branches into the bronchi. The breathing robe includes a plurality of passages with a first passage useful for providing a flow path for the ventilation therapy gas being provided to the ventilated patient and for providing a flow path for removal of exhalation gases. A second passage of the plurality of passages provides a channel for an optical pathway for optical signal transmission to and from a pressure transducer disposed within the second passage closely adjacent the distal end of the endotracheal breathing tube. In one embodiment of the present invention, the second passage and the first passage communicate through an opening between the two passages such that the pressure transducer is exposed to the pressure within the distal end of the endotracheal breathing tube, which in turn is substantially equal to the gas pressure outside the endotracheal tube and thus to the gas pressure at the bronchi of the patient. In another embodiment the pressure sensor is exposed directly to the pressure on the exterior or outer surface of the breathing tube.

Preferably the pressure sensor is of the fiber optic type so that the gas pressure sensed by the pressure transducer and any changes therein are transmitted substantially at the speed of light, i.e., instantaneously, to a control unit that calculates the instantaneous pressure and provides a real time sensing of the pressure in the patient's lungs and any subsequent changes therein. Ventilation of the patient can therefore be better controlled than in prior art sensing technologies in that the ventilator can respond much faster than before to gas pressure changes indicating the patient is inhaling or exhaling, thereby reducing patient/ventilator asynchrony and patient effort in breathing while using the ventilator.

These and other features and advantages of the present invention will become apparent to those skilled in the art when the following detailed description of the invention is read in conjunction with the accompanying drawings and claims. Throughout the drawings, like numerals refer to similar or identical parts.

DETAILED DESCRIPTION OF THE INVENTION

Figure 1:
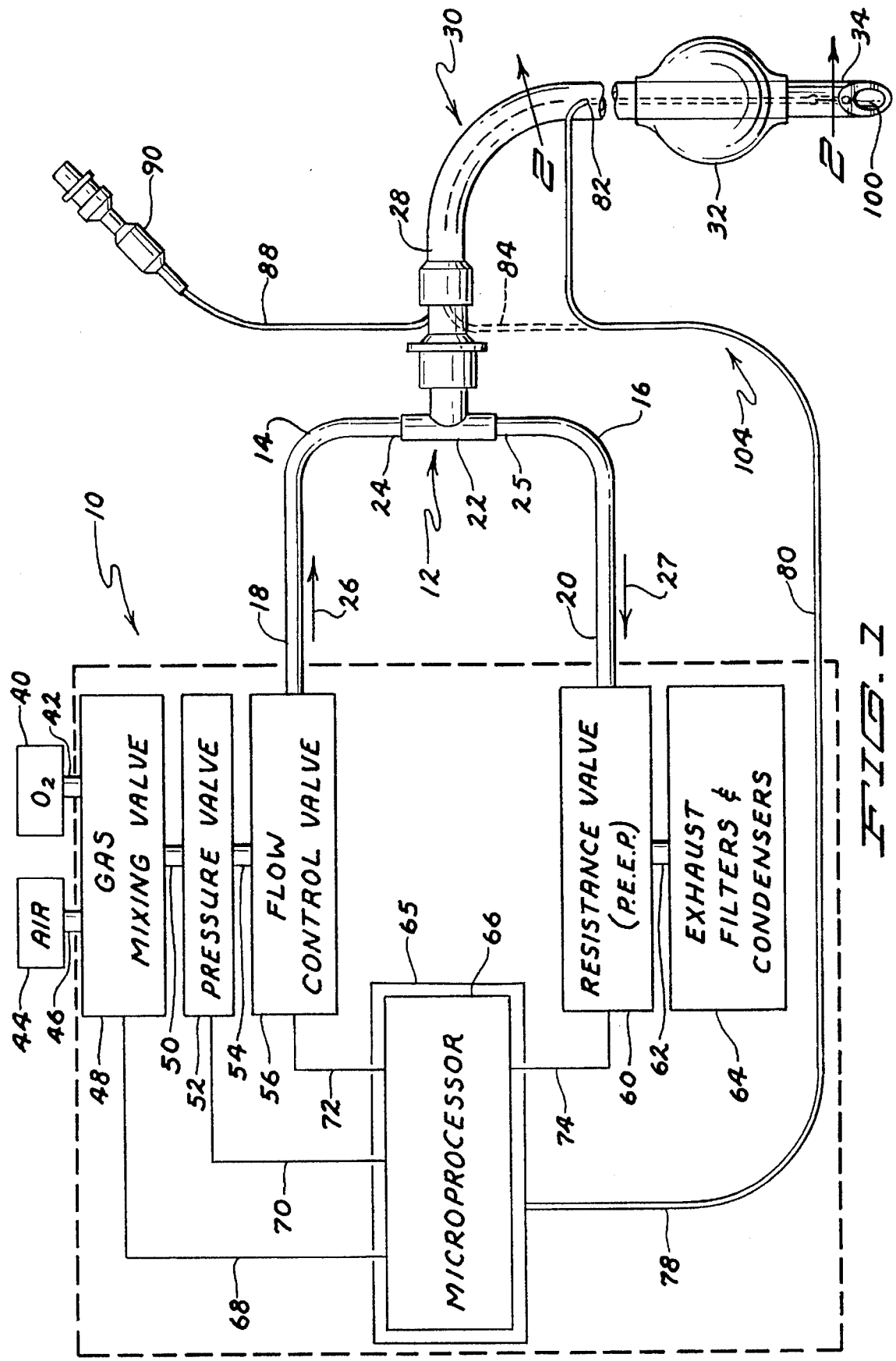
FIG. 1 illustrates in a schematic view a patient ventilation apparatus including an endotracheal breathing tube having a distally mounted pressure sensor in accordance with the present invention.
Figure 4:
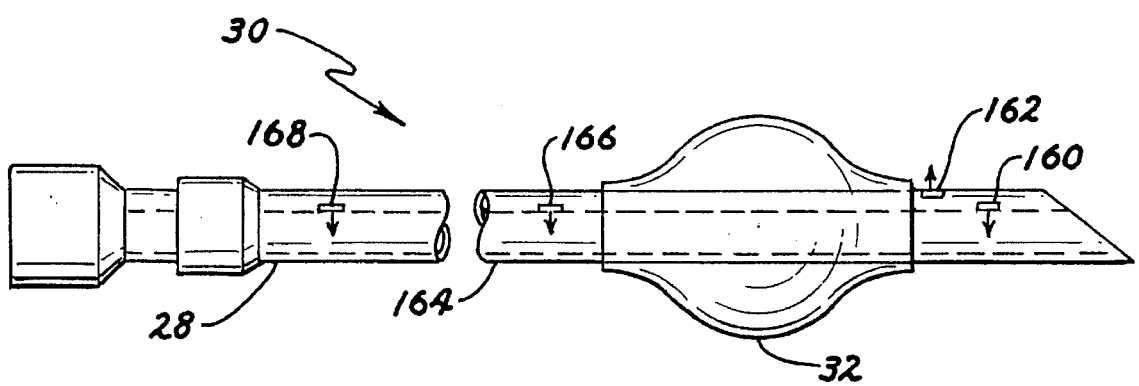
FIG. 4 illustrates alternative locations for an endotracheal breathing tube pressure transducer in accordance with the present invention.

FIG. 1 shows in a schematic view a ventilator 10 and attached airway and breathing tubes useful in accordance with the present invention. Ventilator 10 is attached to an airway tube 12 having a pair of branches 14 and 16. Branch 14 is attached at its proximal end 18 to ventilator 10, while branch 16 is attached at its proximal end 20 to ventilator 10. Branches 14 and 16 are connected to a T-coupling 22 at their distal ends 24 and 25, respectively. Branch 14 is used to supply a ventilation gas to the patient as indicated by arrow 26, while branch 16 is used for the removal of exhalation therapy gases from the patient as indicated by arrow 27. Coupling 22 is connected at its other end to the proximal end 28 of endotracheal breathing tube 30. As shown in FIG. 1, endotracheal breathing tube 30 may, but need not, include a balloon cuff 32 located near the distal end 34 of breathing tube 30. Breathing tube 30 may have beveled end 36 as best seen in FIG. 4.

On the inhalation side, ventilator 10 is usually connected to an oxygen supply 40 by a gas line 42 and to an air supply 44 by a gas line 46. Ventilator 10 includes a gas mixing valve 48 that receives air from air supply 44 via passage 46 and oxygen from oxygen supply 40 via passage 42 and mixes them in the appropriate preselected ventilation therapy ratios. As previously noted, medication may also be included in the ventilation therapy gas supplied to the patient, though the means for doing so will not be discussed herein as it is well known in the art. This mixture which comprises the ventilation therapy gas inhaled by the patient, is supplied by means of a line 50 to a pressure valve 52. Pressure valve 52 controls any mixing of the oxygen and the air and the pressure of the ventilation therapy gas supplied to the patient through branch 14. Pressure valve 52 is connected by a line 54 to a flow control valve 56. Flow control valve 56 controls the volume of gas being supplied to branch 14 of airway tube 12. Airway tube 12 is in turn connected by known means to flow control valve 56. On the exhalation side of ventilator 10, exhaust branch 16 is connected by known means to a resistance valve 60, which measures the patient's peak expiratory end pressure (P.E.E.P.) and which in turn is connected via a line 62 to the appropriate exhaust filters and condensers 64 used to cleanse and filter the exhalation gases before it is released back into the atmosphere.

Ventilator 10 further includes a control and calculation unit 65. Unit 65 comprises microprocessor 66 that controls the operation of gas mixing valve 48 over line 68, pressure valve 52 over line 70, flow control valve 56 over line 72, and resistance valve 60 over line 74. Microprocessor 66 through the appropriate programming controls the operation of valves 48, 52, 56 and 60 based upon pressure sensed by a pressure transducer to be described below. Actual valve operation is accomplished by well known means such as a solenoid and will not be described further. In the embodiment to be described below, a signal is transmitted to control and calculation unit 65 via an interior fiber optic cable 78.

Cable 78 in turn is in light communication with an exterior fiber optic cable 80. For convenience and because the technology is well known, the connector between cables 78 and 80 is not shown. Control and calculation unit 65 further includes a light source, such as a light or laser emitting diode, that is used to provide the light signal transmitted via optical cables 78 and 80. Optical cable 80, as will be explained with reference to FIGS. 2 and 3, enters endotracheal tube 30 and travels through a passage therein to a pressure sensor at the distal end 34 of breathing tube 30. As shown in the Figures, optical cable 80 may either exit breathing tube 30 at a location between the balloon cuff and the proximal end 28 as indicated by reference numeral 82, or as shown in phantom by reference numeral 84, may enter the endotracheal breathing tube 30 at its proximal end connection 28 to T-coupling 22. Also shown in FIG. 1 is a cuff inflation tube 88 that extends, as is well known in the art, from the proximal end 28 of breathing tube 30 to balloon cuff 32. Cuff inflation tube 88 in turn has appropriate couplings 90 disposed at the end thereof for attachment to an appropriate air supply to inflate cuff 32.

Ventilator 10 functions as a pressure compensation to control the volume and pressure of the ventilation therapy gas provided to the patient. Control and calculation unit 65 provides a light signal to a pressure transducer and receives a return light signal therefrom. Control and calculation unit 65 compares the intensity of the transmitted and returned signal and calculates the gas pressure sensed by the pressure transducer. Microprocessor 66 then sends the appropriate signals to valves 40, 52 and 60 based upon an appropriate algorithm so as to properly control the operation of the valves and so as to properly and timely ventilate the patient. Ventilator 10 as is well known, will usually include a signal display and the appropriate controls.

Figure 2A:
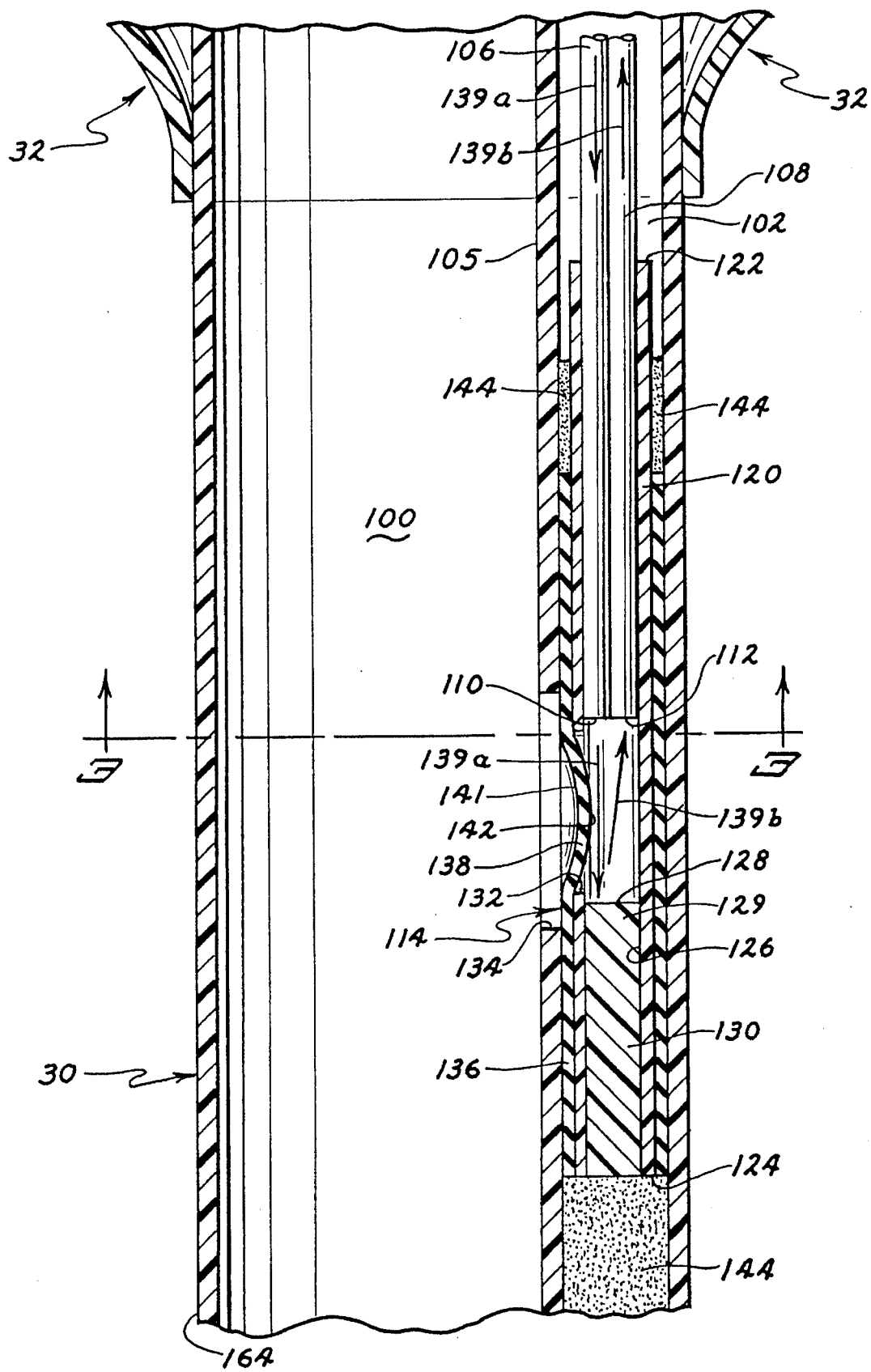
FIG. 2A illustrates in cross section in a partial plan view the portion of the endotracheal breathing tube depicted in FIG. 1 below the balloon cuff.
Figure 2B:
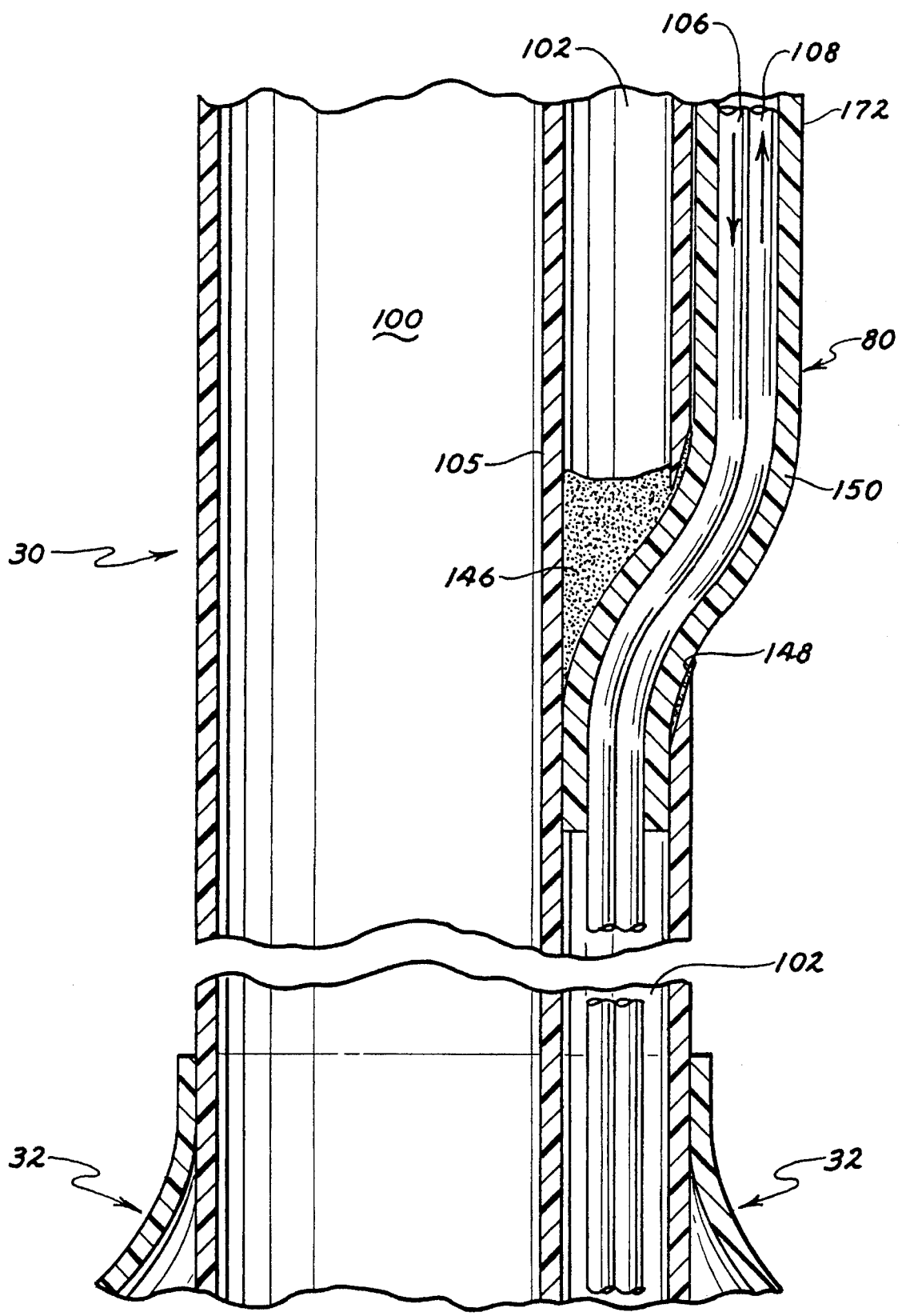
FIG. 2B illustrates in cross section in a partial plan view a portion of the endotracheal breathing tube depicted in FIG. 1 above the balloon cuff and shows the optical pathways exiting the endotracheal breathing tube.

Referring now to FIGS. 2A and 2B, endotracheal tube 30 will be further described. FIG. 2B is a partial cross sectional view of the endotracheal tube 30 showing the entrance/exit of optical cable or lumen 80 from the endotracheal tube 30 and also shows in partial view the balloon cuff 32. Endotracheal tube 30 includes a plurality of passages, here two as indicated by reference numerals 100 and 102, that are preferably non-communicating except as hereafter described. First passage 100 serves as the flow path for the ventilation therapy gases provided to the patient and as the flow path for the exhalation or expiration of breath from the lungs of the patient. Second passage 102 serves as the passage for the appropriate positioning of a pressure transducer 104. In the embodiment shown in FIGS. 2–3, second passage 102 is formed entirely within a thickened wall portion of breathing tube 30 and is substantially fully enclosed the entire length of breathing tube 30. The space in passage 102 is typically maintained at ambient atmospheric pressure during measurements by being in communication with the atmosphere at the proximal end of cable 78 inside control and calculation unit 65. This is important in measuring pressures as will be described below in further detail. First and second passages 100 and 102 each have a substantially tubular configuration and are separated by a wall 105.

The pressure transducer 104 is preferably of the fiber optic type. This type of pressure sensor will be described below; however, a pressure sensor such as known solid state types of devices that also respond nearly instantaneously could also be used in accordance with the present invention. The fiber optic type of pressure transducer converts sensed pressure variations into a light modulated signal. The device is calibrated so that the light signal is proportional to pressure. An optical pathway is the preferred mode of light transmission from a light source usually disposed within ventilator 10 to the pressure sensor and back to ventilator 10. This optical pathway is usually provided by optical fibers or leads. Such leads may be in the configuration of a single fiber which serves to both send and receive light signals to and from the transducer, in the form of two fiber optic leads where one fiber serves to transmit and one to receive light signals, or in the form of a fiber bundle. The dual lead configuration is preferred and is disclosed herein, reference numerals 106 and 108 indicating a pair of elongated, parallel fiber optic leads which extend longitudinally within second tubular passage 102. The proximal ends of fiber optic leads 106 and 108 terminate within a connector (not shown) at ventilator 10, and their distal ends 110 and 112, respectively, terminate within a pressure transducer assembly 114. Passage 102 thus serves as a passage for the transmission of pressure indicating signals from pressure transducer assembly 114 (FIG. 2A), which is mounted at the distal end 34 of endotracheal tube 30. The connector at ventilator 10 serves to connect the transducer leads 106 and 108 to lead 78, which in turn is connected to control and calculation unit 65 and, hence, to microprocessor 66, which, as noted, provides an output signal to a display on ventilator 10. Fiber optic lead 106 serves as a light signal transmitting path for transmitting light from the light source at control unit 65 to the pressure transducer assembly 114. Fiber optic lead 108 serves to convey light signals from the pressure transducer assembly 114 back to the control unit 65.

Figure 3:
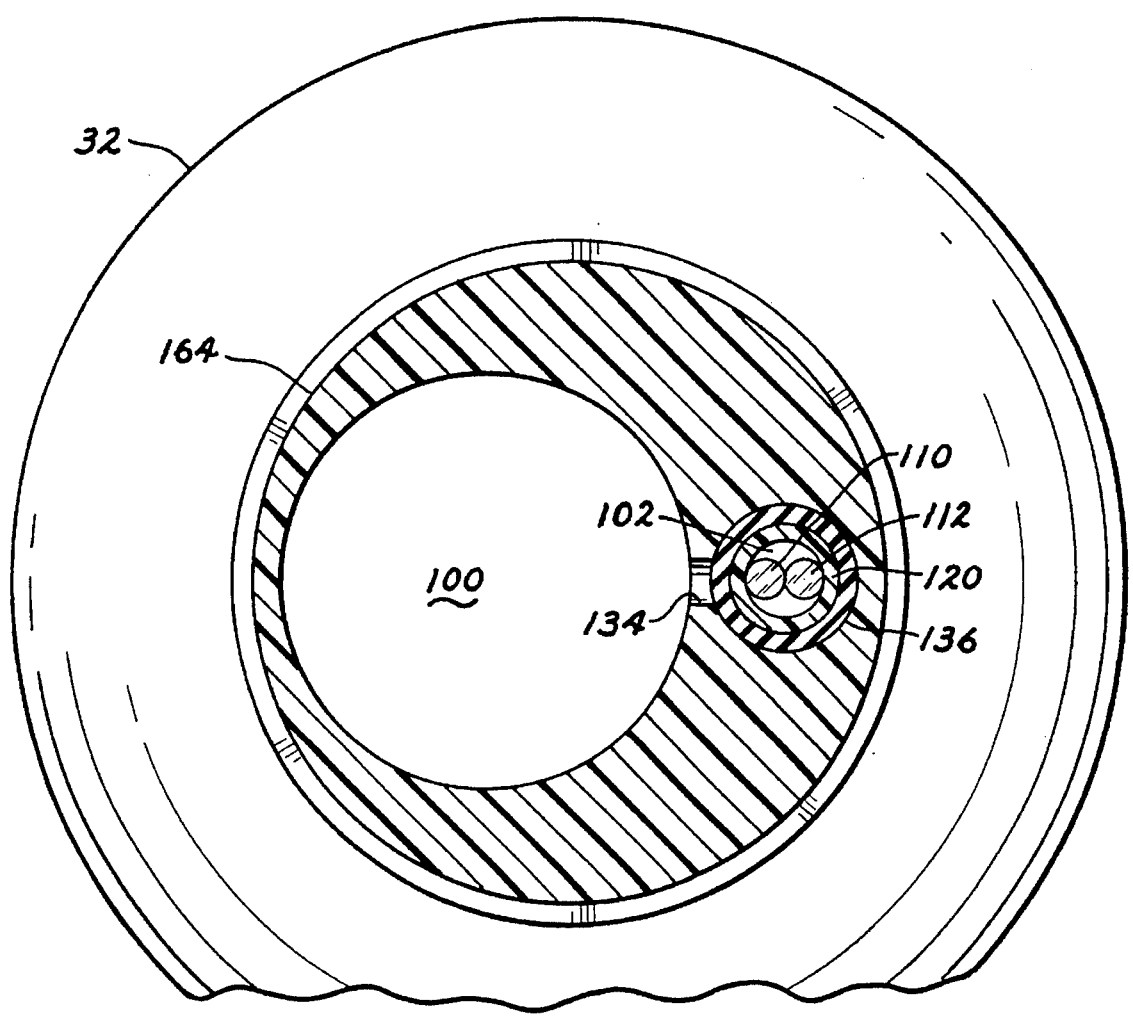
FIG. 3 shows the endotracheal breathing tube shown in FIGS. 1, 2A and 2B in a cross sectional view taken along cutting plane 3—3 of FIG. 2A.

The transducer assembly 114 includes a housing 120 which is wholly contained within second passage 102 near the distal end thereof. Housing 120 may be made from metal or plastic. Housing 120 is preferably made of stainless steel. Alternatively, biocompatible, rigid plastic, such as polycarbonate, acrylic, or polyurethane, could be used. Housing 120 is shown most clearly in the side elevation cross section view of FIG. 2A and the end elevation cross section view of FIG. 3. It is preferably of a hollow cylindrical shape, and has opposed proximal and distal ends 122 and 124, respectively. Housing 120 receives the distal ends 110 and 112 of fiber optic leads 106 and 108 in the manner shown in FIGS. 2A and 3. The end of housing 120 adjacent to distal end 124 is hollow or open as shown in FIGS. 2A and 3 to provide a cavity 126 within which light signals may be transmitted between the distal ends 110 and 112 of the first and second fiber optic leads 106 and 108. For that purpose, in the preferred embodiment as disclosed herein, a reflector 128 is utilized. Reflector 128 comprises a reflective surface which may be integral to, formed on or applied to the proximal end 129 of an end plug 130. As shown in the drawings, reflector 128 has a substantially planar or flat surface. If desired, end plug 130 may be formed so as to provide a concave recess on its inner end which forms a segment of a sphere, which serves as reflector 128. While such concave surfaces can be used as the reflector, they present some problems in their use in that their focal length must be considered and thus the distance of the concave surface from the distal ends 110 and 112 of fibers 106 and 108 must be carefully adjusted so as to take into account the focusing properties of the concave reflective surface.

End plug 130 has a substantially cylindrical configuration and is received within the cavity 126 at the distal end 124 of housing 120 and retained therein by known means. End plug 130 may be made out of metal or plastic. If end plug 130 is made out of plastic, preferably relatively hard reflector surface 128 may comprise a metal surface electroplated thereon, or a hot stamped, reflective coating applied to the proximal end of end plug 130. If end plug 130 is made of metal, such as titanium or stainless steel, reflector surface 128 may comprise a polished surface on the proximal end of plug 130 or reflector 128 may comprise a reflective material, such as gold, which has a higher degree of reflectance relative to the frequency of transmitted visible red light, plated to the distal end of end plug 130. As also appears most clearly in FIG. 2A, housing 120 is molded or cut out to the configuration shown so as to provide an aperture 132 along that side of housing 120 adjacent first passage 100.

An opening 134 is made in the wall 105 adjacent to aperture 132. As shown in the drawings, opening 134 has a configuration conforming in configuration but of larger extent than the outer perimeter of the aperture 132 formed in housing 120. Such a configuration is not required by the present invention. For example, it may be advantageous to make opening 134 such that it has a smaller size than that of aperture 132. Furthermore, in some embodiments it may be desirable to cover opening 134 with a screen or gel of some type. Opening 134 in the wall 105 serves as an aperture or port for pressure sensing and is preferably the only means of communication between passages 100 and 102.

For the purpose of sensing changes in pressure, a flexible membrane 136 is positioned on the housing 120. Flexible membrane 136 is disposed in covering relation to the aperture 132, adjacent to the wall opening 134. The portion of flexible membrane 136 which overlies the aperture 132 in the housing 120 is a pressure-sensitive segment 138 which is free to flex or deflect transversely with respect to the path of light passing longitudinally between fiber optic lead distal ends 110 and 112 via reflector 128. Membrane 136 may take the form of a patch or, as shown, a sleeve. Preferably, as may be noted most clearly by reference to FIG. 2A, membrane 136 is in the form of a cylindrical sleeve embracing the housing 120 in a snug fit therewith. The material of the membrane sleeve is preferably elastomeric, and could be urethane or silicone. In addition, it is also known in the art to use membranes made of a metallic material. These metallic membranes may also be used with the present invention.

As a particularly beneficial feature, flexible membrane 136 is secured around the outside of housing 120 over the aperture 132 cut therein so as to be placed in tension in a prestressed condition. For that purpose, membrane sleeve 136 prior to installation over housing 120 has an inner diameter less than the preferred outside diameter of housing 120. Membrane sleeve 136 is stretched so as to get it over housing 120. Alternatively, a silicone membrane sleeve 136 may be placed in a solution which causes it to dilate, after which it is slipped over the end of the housing 120 in covering relation to the aperture 132. The membrane sleeve then returns to its undilated state as the solution evaporates. Freon has been found to be satisfactory for use as a dilating solution. In either case, the membrane sleeve 136 is prestressed in tension around housing 120 and over the aperture 132. This causes the membrane to be initially set at an inwardly flexed condition in which pressure responsive segment 138 thereof is curved inwardly. As shown in FIG. 2A, pressure responsive segment 138 assumes somewhat the shape of a segment of a sphere in its inwardly curved set position. The membrane sleeve is placed in tension a predetermined extent so that segment 138 will have an inward, sufficient deflection that segment 138 will extend slightly into the linear path of light traveling between distal ends 110 and 112 of fiber optic leads 106 and 108, respectively, via reflector 128. Segment 138 is free to flex either inwardly or outwardly. Thus, because of its initial, inward deflection partially blocking the flow of light through the fiber optic, light-transmitting circuit and because passage 102 and gap 140, in communication with 102, is at atmospheric pressure, as described earlier, it is able to sense negative pressures or pressures below atmospheric pressure within the body of a patient. Thus, if the pressure being sensed externally of pressure transducer assembly 114 on the outer surface of membrane segment 138 decreases, the membrane will flex slightly outwardly to permit a greater passage of light between the distal ends 110 and 112 and reflector 128. This change in light transmission will be sensed as a signal indicating a decrease or negative change in pressure.

The deflection of membrane segment 138 in response to changes in the pressure differential across its inner and outer surfaces is assured by connecting the underside or inner face of membrane segment 138 to an atmospheric or other reference pressure. That is, second passage 102 is at atmospheric or a known reference pressure.

As shown in FIG. 2A, reflector 128 is spaced apart from distal ends 110 and 112 of the two fiber optic paths, in opposing relation thereto. Thus, light signals conducted by fiber optic lead 106 are directed from distal end 110 onto the surface of reflector 128, and are reflected back thereby to distal end 112 of fiber optic return path 108. Arrows 139a and 139b within fiber optic leads 106 and 108 indicate such light transmission to and from reflector 128, respectively. The length of the gap 140 between fiber optic distal ends 110 and 112 and the surface of reflector 128 is predetermined so as to optimize light signal transmission. The operation of the pressure transducer is believed to be clearly understood from the foregoing description. The outer surface 141 of pressure-responsive segment 138 of membrane 136 exterior of housing 120 is exposed to pressure within the body of a patient, that is, in the patient's trachea. The inner surface 142 of membrane segment 138 is exposed to pressure inside of housing 120, which will normally be atmospheric pressure, though as noted, a standard reference pressure may be used. Thus, any pressure increase within a patient[<b]old3 s body as sensed on the outside surface 141 of pressure responsive segment 138 of membrane 136 will cause segment 138 to deflect inwardly into the gap 140 provided between distal or terminal ends 110 and 112 of fiber optic leads 106 and 108 and the reflector 128. The passage of light across gap 140 between distal end 110 and reflector 128 will thus be more obstructed or restricted, and this change in light transmission will be reflected to distal end 112 of lead 108 as a return signal indicative of an increase in pressure within a patient's body. Any decrease in pressure within the patient's body as sensed on the outside surface 141 of membrane segment 138 will cause that membrane to deflect more outwardly, and thus permit more light to pass across the gap 140 to distal end 112 of lead 108. A return signal to fiber optic lead 108 indicative of a pressure decrease will thus be transmitted to ventilator 10 and thus to control and calculation unit 65.

Figure 6:
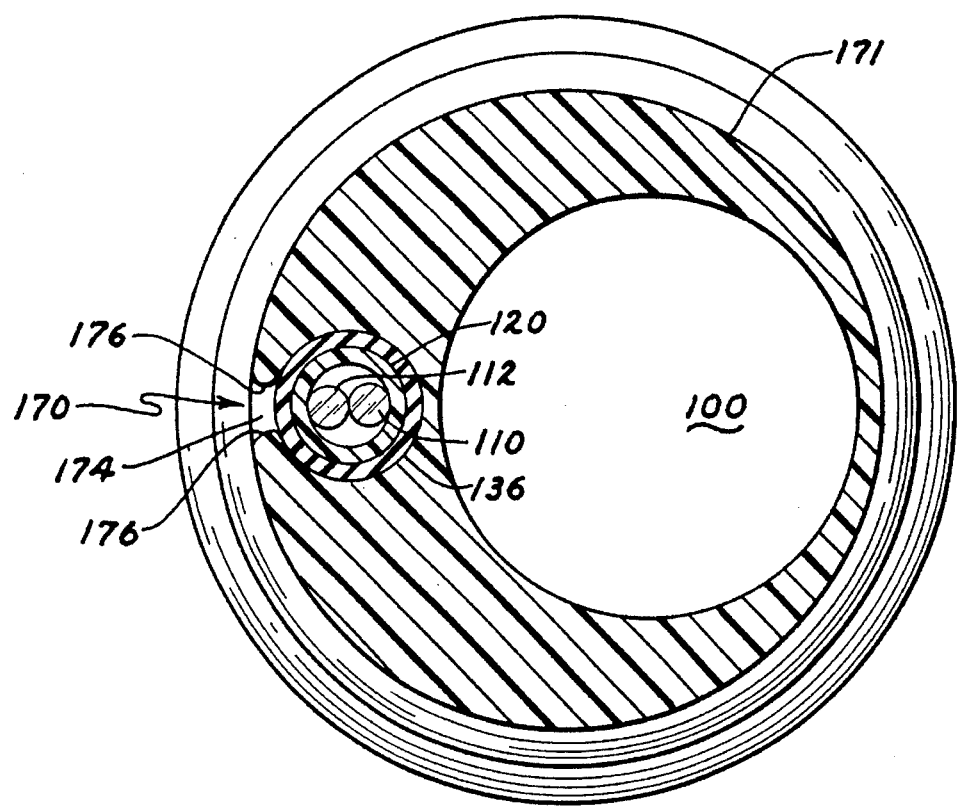
FIG. 6 shows a cross sectional view taken along cutting plane 6—6 of FIG. 5 and shows the pressure transducer and light conducting fibers are disposed within the groove running along the exterior surface of the breathing tube.
Figure 5:
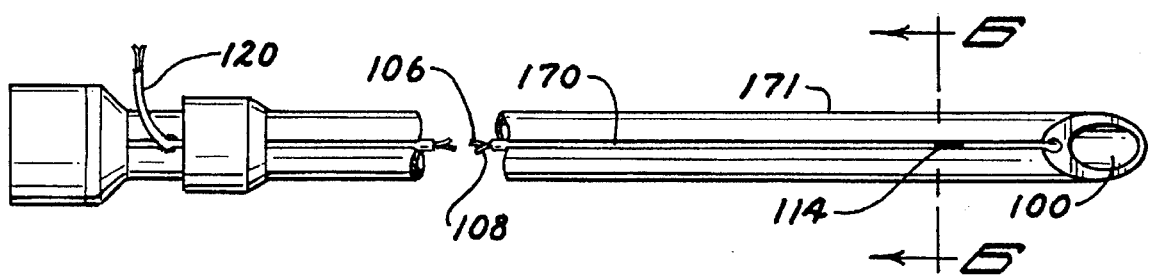
FIG. 5 illustrates an alternative embodiment of an endotracheal breathing tube in accordance with the present invention and shows the groove running the length of the breathing tube.

Housing 120 is held in place at both ends by suitable potting or cementing material 144 as is well known in the art. This potting or cementing material 144 also serves to isolate the atmospheric pressure inside passage 102 from the outside pressure on surface 141 of segment 138 of membrane 136. Similarly, as seen in FIG. 2B, potting 146 is used to seal off second passage 102 where optical cable 80 exits second passage 102. Thus, second passage 102 and therefore endotracheal tube 30 includes an opening 148 therein wherein optical cable 80 exits and enters second passage 102. As shown in the embodiment of the present invention, optical cable 80 includes an outer cover or sheath 150 that circumscribes optical fibers 106 and 108. If desired, cover 150 may terminate after insertion of the optical cable 80 within second passage 102 of endotracheal tube 30. Cover 150 may continue distally to the transducer assembly 114 as seen in FIGS. 5 and 6.

Referring now to FIG. 4, alternative locations of an endotracheal tube pressure transducer are shown. With respect to each of the locations to be discussed below, it should be noted that each location is shown along a single side of the endotracheal breathing tube 30. The particular circumferential position of the pressure transducer is not critical, however. The transducer can be located at any circumferential position relative to endotracheal breathing tube 30 and be within the scope of the present invention. Thus, as indicated in FIG. 4, location 160 for pressure transducer assembly 114 is substantially that location shown in FIGS. 2A and 3. A pressure transducer assembly 114 similar to that shown in FIGS. 2A and 3 could also be located at position 162. At location 162, first and second passages 100 and 102 could be completely non-communicating. At location 162, an opening would be made in the outer surface 164 of endotracheal tube 30. At this location, the pressure differential sensed would be between that of the atmospheric or reference pressure on the inner surface 142 of the pressure sensitive segment 138 of membrane 136 and the pressure on the outer surface 164 of endotracheal tube 30.

A third alternative location for the pressure transducer assembly 114 would be at position 166 which, as shown, is on the proximal side of the balloon cuff 32. In all other respects, the pressure transducer 104 and transducer assembly 114 would be substantially similar to that at preferred location 160. Finally, a fourth location for a transducer assembly 114 would be as shown at 168 which is substantially adjacent the proximal end 28 of endotracheal tube 30.

It should be noted that where the pressure transducer assembly is to be located proximally of balloon cuff 32 that its location must always be such that the pressure being sensed is that in the first passage 100. That is, because balloon cuff 32 will substantially close off the trachea, if the pressure assembly 114 were located at locations 166 or 168, it would sense the pressure on the outside surface 164 of endotracheal tube 30, as does the transducer assembly at location 162. Thus, a false pressure reading would be given since the portion of the endotracheal tube 30 distally displaced from balloon cuff 32 is pressure un-coupled from the portion of endotracheal tube 30 proximally placed of balloon cuff 32. Where the transducer assembly is disposed distally of the balloon cuff 32, it may be placed such that the pressure being sensed is either internal of first passage 100 or external on surface 164 of endotracheal tube 30.

In some instances where ventilation therapy is used it is necessary to trim or shorten the endotracheal tube at its proximal end to fit the needs of the particular patient care situation. Thus, FIGS. 5 and 6 show an alternative embodiment of the present invention wherein optical cable 80 is disposed within a second passage taking the form of a groove 170 formed in the outer surface 164 of an endotracheal tube 171. Groove 170 has a substantially circular configuration to conform to the outer surface 172 (FIG. 2B) of optical cable 80, whose sheath 150 will be carried substantially to pressure transducer assembly 114 rather than terminate as shown in FIG. 2B. Groove 170 may, as shown, be substantially open to the outer environment or it may, if desired, be only partially opened thereto. As seen in FIG. 5, groove 170 has an opening 174 that is narrower than its diameter so as to form a pair of flexible flaps 176 that may be spread apart to insert the optical cable 80 and that then return to their normal configuration tightly holding the optical cable 80 and pressure transducer assembly 114 in place. In this embodiment pressure transducer assembly 114 will be rotated 180° from the position shown in FIG. 2A such that the pressure sensitive member is exposed to the pressure on the outside of the breathing tube 30. Thus, with the embodiment shown in FIGS. 5 and 6, the endotracheal breathing tube may be trimmed to the desired length and the optical cable 80 with the attached fiber optic pressure transducer assembly 114 may be inserted into groove 170. Groove 170 may also be formed in the embodiment of breathing tube 30 shown in FIGS. 2–4 and used as a channel for disposing other sensors, such as temperature or gas measurement sensors.

The endotracheal breathing tube shown in FIGS. 5 and 6 is shown without a balloon cuff. As is well known in the art, endotracheal tubes intended for use by adults usually have such cuffs while those intended for use children, including infants, may not have them. The present invention is useful with cuffed and uncuffed as well as trimmable and untrimmable types of endotracheal breathing tubes.

With the present invention then, administration of ventilation therapy can be improved for several reasons. Changes in pressure in the lungs can be quickly sensed and the sensed change in pressure transmitted substantially instantaneously to the control unit 65 in ventilator 10 so as to activate either the inhalation or exhalation side of the ventilation cycle as is appropriate. In addition, this rapid sensing and transmission of the sensed pressure enables the ventilator to compensate and control the pressure changes within the patient's lungs. As previously noted, this can be critical, since barotrauma is a common concern with all patients, but especially with respect to an infant where over-pressurization can result in substantial damage to the infant's undeveloped lungs. Furthermore, because of the rapid response time with the present invention, patient/ventilator asynchrony and patient effort in breathing while being ventilated is reduced, thereby conserving the patient's energies for the healing process. In addition, disposing the pressure sensor at the distal end of the breathing tube provides an inherently more accurate measurement of the pressure within the patient's lungs because of the close proximity of the sensor thereto. Preliminary testing of an embodiment of the present invention indicates that a typically positioned transducer outside the patient's body can indicate a pressure of seventy (70) inches of water whereas the present invention will indicate at the same time a pressure of fifteen (15) inches of water near the patient's lungs. This preliminary result clearly indicates the enhanced benefit of monitoring pressures as close to the lungs as possible. These preliminary tests were conducted using a type of artificial lung known in the industry for such testing. Lastly, because of the rapid response in the breathing circuit cycle of the present invention, the alveoli of the lungs are more effectively ventilated, thereby increasing the benefits of the ventilation therapy and reducing patient recovery time.

It is anticipated that various changes can be made in the size, shape, and construction of the endotracheal tube mounted pressure transducer assembly disclosed herein without departing from the spirit and scope of the invention as defined by the following claims:

What is claimed is:

1. Apparatus for providing improved ventilation of a patient, said apparatus comprising:

an endotracheal breathing tube comprising first and second passages, said breathing tube and said first and said second passages having distal and proximal ends, said distal end of said breathing tube being configured for disposition in the patient's trachea;

an airway tube for supply of at least one ventilation gas to said first passage and for removal of exhalation gases from the patient, said airway tube being connected at one end to a supply of at least one ventilation gas and at the other end to said proximal end of said first passage;

said first passage providing a flow path for the at least one ventilation gas between said airway tube and the patient;

ventilator means for controllably ventilating the patient with the at least one ventilation gas;

wherein said apparatus further includes a sensor for sensing pressure within the patient's trachea, said sensor being disposed on said distal end of said breathing tube and providing real-time sensing of the gas pressure within the patient's trachea, said sensor being in communication with said ventilator means;

said sensor comprising:
  a pressure transducer; and
  an optical path extending longitudinally within said second passage of said breathing tube and defining a light transmitting circuit comprised of optical fiber lead means for transmitting light along said optical path from an external source to said pressure transducer and from said pressure transducer to said ventilator means, said path having a distal end and a proximal end; and
  wherein said pressure transducer is mounted at said distal end of said optical path and of said breathing tube such that it senses the pressure within the patient's trachea and comprises:
    a housing disposed within said second passage and receiving and holding said distal end of said optical path in predetermined position in optical coupling relation with itself, said housing having an aperture disposed distally of said distal end of said optical path; and
    a flexible membrane on said housing disposed in covering relation to said aperture, said membrane having a pressure responsive segment extending over said aperture and exposed to the pressure inside of the patient's trachea on its outer surface and to pressure inside of said housing on its inner surface, said pressure responsive segment of said membrane being movable transversely across said aperture in response to changes in pressure inside said first passage to thereby change light transmission through said distal end of said optical path, and said membrane is a cylindrical sleeve embracing said housing in a snug fit therewith;

whereby said ventilator means controls the ventilation of the patient in response to the sensed gas pressure in said breathing tube.

2. The apparatus of claim 1 wherein said sensor is of the type having an extended optical fiber path for light transmission to and from said sensor.

3. The apparatus of claim 1 wherein:
said housing is of generally hollow, cylindrical shape.

4. The apparatus of claim 1 wherein:
the inner surface of said pressure responsive segment of said membrane is coupled to atmospheric pressure.

5. The apparatus of claim 1 wherein:
said membrane sleeve is of elastomeric material and is stretched over said aperture in said housing so as to be in tension with said pressure responsive segment thereof being deflected through and away from said opening and into said aperture, whereby said pressure responsive segment will deflect outwardly in response to a decrease in pressure in said first passage and thus present less of an obstruction to light transmission across said aperture.

6. The apparatus of claim 1 and further comprising:
a reflector spaced apart from said distal end of said optical path a predetermined distance in opposing relation thereto, and said distal end of said path is optically coupled to itself by said reflector whereby light signals from said distal end of said path will be reflected back to said distal end of said path.

7. The apparatus of claim 6, and further comprising:
an end plug having distal and proximal ends, said end plug closing said distal end of said housing; and
said reflector comprises a reflective surface on said proximal end of said plug.

8. The apparatus of claim 1 wherein said breathing tube includes an opening extending between said first and second passages, said pressure transducer being disposed within said second passage such that said aperture is adjacent to said opening and such that said membrane is exposed to the pressure inside of said first passage.

9. The apparatus of claim 1 wherein said optical path comprises at least first and second optical fibers, said first and second fibers having proximal and distal ends, said first fiber being a light transmitting pathway for transmitting light to said pressure transducer and said second fiber being a light transmitting pathway for transmitting light from said pressure transducer to said ventilator means.

10. The apparatus of claim 1 and further comprising an inflatable balloon cuff for releasable placement of said breathing tube distal end at a preselected location within the patient's trachea, said cuff being located adjacent said breathing tube distal end.

11. The apparatus of claim 10 wherein said sensor is disposed relatively closer to said breathing tube distal end than said balloon cuff is disposed.

12. The apparatus of claim 1 and further comprising a pressure compensator, said compensator being provided for varying the pressure of the at least one ventilation gas supplied to the patient in correspondence with the patient's respirations; and means for supplying the sensed pressure to said pressure compensator.

13. The apparatus of claim 12 wherein said ventilator means includes:

calculating means for calculating the pressure within the patient's trachea, said calculating means using the pressure sensed by said sensor to calculate the gas pressure within the patient's trachea; and valve means for varying the pressure of the at least one ventilation gas within the breathing tube in response to the calculated pressure, said valve means being disposed between a supply of ventilation gas and said airway tube;

whereby said pressure sensor provides a pressure indicating signal to said calculating means, which controls pressurization of the patient's lungs during ventilation of the patient.

14. The apparatus of claim 1 wherein said ventilator means includes:

calculating means for calculating the pressure within the patient's trachea, said calculating means using the pressure sensed by said sensor to calculate the gas pressure within the patient's trachea; and valve means for varying the pressure of the at least one ventilation gas within the breathing tube in response to the calculated pressure, said valve means being disposed between a supply of ventilation gas and said airway tube;

whereby said pressure sensor provides a pressure indicating signal to said calculating means, which controls pressurization of the patient's lungs during ventilation of the patient.

15. The apparatus of claim 1 wherein said second passage comprises a groove extending substantially the length of said breathing tube along the outer surface thereof.

16. The apparatus of claim 1 wherein said optical path comprises at least first and second optical fibers, said first and second fibers having proximal and distal ends, said first fiber being a light transmitting pathway for transmitting light to said pressure transducer and said second fiber being a light transmitting pathway for transmitting light from said pressure transducer to the ventilator means.

17. The apparatus of claim 1 wherein said breathing tube is comprised of a substantially cylindrical wall having inner and outer surfaces, said first passage being substantially defined by said inner wall surface and providing a flow path for the at least one ventilation gas between said airway tube and the patient, said second passage being disposed within said wall between said inner and outer surfaces thereof.

* * * * *

UNITED STATES PATENT AND TRADEMARK OFFICE
CERTIFICATE OF CORRECTION

PATENT NO. : 5,546,935
DATED : August 20, 1996
INVENTOR(S) : Champeau

It is certified that error appears in the above-identified patent and that said Letters Patent is hereby corrected as shown below:

At col. 8, line 38, delete "patient [ <b]old3 s" and insert --patient's--.

Signed and Sealed this

Fifteenth Day of September, 1998

Attest:

BRUCE LEHMAN

*Attesting Officer*   *Commissioner of Patents and Trademarks*